(12) United States Patent
Rudas

(10) Patent No.: US 7,211,429 B1
(45) Date of Patent: May 1, 2007

(54) ORGANIC WASTE MATERIAL TREATMENT PROCESS

(75) Inventor: Tomasz Rudas, Darlington (AU)

(73) Assignee: Organic Resource Technologies Limited, Bentley (AU)

( * ) Notice: Subject to any disclaimer, the term of this patent is extended or adjusted under 35 U.S.C. 154(b) by 150 days.

(21) Appl. No.: 10/031,421

(22) PCT Filed: Jul. 20, 2000

(86) PCT No.: PCT/AU00/00865

§ 371 (c)(1),
(2), (4) Date: Jan. 18, 2002

(87) PCT Pub. No.: WO01/05729

PCT Pub. Date: Jan. 25, 2001

(30) Foreign Application Priority Data

Jul. 20, 1999 (AU) .................................... PG1740

(51) Int. Cl.
*C05F 11/08* (2006.01)
*C12P 5/02* (2006.01)

(52) U.S. Cl. .................. 435/262; 435/167; 435/300.1; 71/9; 71/10; 210/603; 210/613; 210/630; 48/197 A

(58) Field of Classification Search ............. 435/262, 435/262.5, 252.4, 267, 289.1, 290.1, 290.4, 435/300.1, 42, 166, 167; 71/8–10; 210/603, 210/605, 612, 613, 630; 405/128.5, 129.25, 405/129.95; 48/197 A
See application file for complete search history.

(56) References Cited

U.S. PATENT DOCUMENTS

| | | | | |
|---|---|---|---|---|
| 2,337,686 A | * | 12/1943 | Sherman | .......... 71/9 |
| 3,895,916 A | * | 7/1975 | Rosner | .......... 422/242 |
| 4,565,552 A | * | 1/1986 | Cotton | .......... 48/197 A |
| 4,699,548 A | * | 10/1987 | Bergstrom | .......... 406/109 |
| 4,837,153 A | * | 6/1989 | Laurenson, Jr. | .......... 435/243 |
| 5,447,850 A | * | 9/1995 | McCann | .......... 435/42 |

FOREIGN PATENT DOCUMENTS

| | | | |
|---|---|---|---|
| DE | 4124880 A1 | * | 1/1993 |
| DE | 4409487 A1 | * | 4/1995 |
| DE | 44 40 750 C1 | | 5/1996 |
| EP | 0 755 905 A1 | | 4/1996 |
| FR | 2288719 A | * | 6/1976 |
| WO | PCT/DE94/00440 | | 4/1994 |

OTHER PUBLICATIONS

Dersent Abstract Accession No. 98-571533/49; JP 10-249386 (NGK Insulators Ltd.) Sep. 22, 1998.
Dersent Abstract Accession No. 98-012790/02; JP 10-277585, (Matsushita Electric Works, Ltd.), Oct. 1998.
Dersent Abstract Accession No. 98-363083/47; JP 07-246395, (ZH Nihon Jogyo Shuraku Haisui Kyokai) Sep. 26, 1995.

* cited by examiner

*Primary Examiner*—William H. Beisner
(74) *Attorney, Agent, or Firm*—Duane Morris LLP

(57) ABSTRACT

An organic waste material treatment process comprising subjecting the organic waste material to conditions under which anaerobic digestion occurs followed by conditions under which aerobic composting occurs. Preferably, the organic waste material is pre-conditioned before anaerobic digestion by subjecting the organic waste material to aerobic composting conditions to facilitate a rise in temperature of the organic waste material. The treatment process is conducted in a single vessel, wherein air and water are evenly distributed to the contents of the vessel. A plurality of vessels may be interconnected, such that water may be extracted from one vessel, whose contents have undergone anaerobic digestion, then recirculated to an interconnected vessel to facilitate conditions for anaerobic digestion of the contents of the interconnected vessel.

12 Claims, 2 Drawing Sheets

ORGANIC WASTE MATERIAL TREATMENT PROCESS

FIELD OF THE INVENTION

The present invention relates to an organic waste material treatment process.

BACKGROUND OF THE INVENTION

It is well known that degradation of solid organic waste material to a bioactive, stabilised end product such as compost for gardens, can be achieved by treating the solid organic waste material under either anaerobic or aerobic conditions in which anaerobic or aerobic microorganisms, respectively, metabolise the waste material to the end product.

Aerobic decomposition of solid organic waste material takes place in the presence of oxygen. Energy produced during aerobic decomposition is released as heat, the temperature of the material frequently rising to 75° C. under ambient conditions. The resulting solid end product is generally rich in nitrates which is a readily bioavailable source of nitrogen for plants. Thus the bio-available resultant end product is an excellent fertilising material for gardens and has commercial value as such.

Anaerobic digestion of solid organic waste takes place in the absence of oxygen. Typically, the solid organic waste must be heated to a mesophilic or thermophilic temperature range in order for anaerobic microbial metabolism to be optimised. Energy produced during anaerobic digestion is conserved as biogas, predominantly methane and carbon dioxide. The resultant solid end product is generally rich in ammonium salts.

Ammonium salts are not readily bio-available for uptake by plants. It is known, therefore, to treat residues, resulting from anaerobic digestion, with conditions under which aerobic decomposition will proceed. Thus, the material is converted to one rich in nitrates and which is of commercial value.

Systems have generally been designed to cater discretely for each type of degradation, although some systems have been designed to combine both anaerobic and aerobic decomposition processes.

German Patent Number 4440750 relates to an apparatus for raw material and energy recovery from biomass which has an anaerobic fermentation unit, an aerobic composting unit, a gasification unit and a power generating plant. The apparatus utilises byproducts from the anaerobic fermentation unit and the aerobic composting unit to work synergistically to provide reduced amounts of residues and to improve raw material and energy production.

International Patent Application Number WO 94/24071 discloses treatment of organic bioresidues especially from municipal and industrial wastes, including raw and/or cooked food residues, agricultural wastes and/or plant vegetable components. The bioresidues are first homogenised, fermented in an anaerobic reactor wherein the resulting biogas is removed, and then the residual solids are transferred to a composting chamber.

These and other similar systems provide discrete and separate chambers or vessels for aerobic decomposition and anaerobic digestion, respectively. Material which has undergone one set of conditions is transferred to a separate location to undergo a secondary processing phase. The transfer of material from one location to another is not efficient in terms of time, costs and labour.

The present invention seeks to overcome, at least in part, some of the aforementioned disadvantages.

SUMMARY OF THE INVENTION

In accordance with a first aspect of the present invention there is provided an organic waste material treatment process for organic waste material received in a vessel comprising the steps of:
a) displacing air in the vessel and contents thereof with water to create conditions suitable for anaerobic digestion of the contents to proceed;
b) anaerobically digesting the contents of the vessel by action of anaerobic bacteria;
c) separating gaseous byproducts from residues resulting from step b);
d) removing at least a portion of the water from the vessel;
e) administering air to the residues in the vessel to create conditions suitable for aerobic composting of the residues to proceed;
f) aerobically composting the residues by action of aerobic bacteria; and
g) recovering compost resulting from step f) from the vessel.

In accordance with a second aspect of the present invention there is provided an organic waste material treatment process for organic waste material received in a plurality of interconnected vessels comprising the steps of:
a) displacing air in at least one of the vessels and contents thereof with water received from an interconnected vessel to create conditions suitable for anaerobic digestion of the contents to proceed in the or each vessel, the contents of the interconnected vessel having already undergone anaerobic digestion;
b) anaerobically digesting the contents of the or each vessel;
c) separating gaseous byproducts from residues resulting from step b);
d) removing at least a portion of the water from the or each vessel and transferring the portion of the water to another interconnected vessel for use in step a);
e) administering air to the residues in the or each vessel to create conditions suitable for aerobic composting of the residues to proceed;
f) aerobically composting the residues; and
g) recovering compost resulting from step f) from the or each vessel.

In accordance with a third aspect of the present invention there is provided a vessel for anaerobic digestion and aerobic composting of organic waste material comprising a means for receiving organic waste material, first feed means for supplying water to the vessel and second feed means for supplying air to the vessel, wherein the first and second feed means are arranged to evenly distribute water and air to the organic waste material; the vessel being devoid of any internal agitation means.

In accordance with a fourth aspect of the present invention there is provided an apparatus arranged, in use, to facilitate an organic waste material treatment process, comprising at least one vessel for sequential anaerobic digestion and aerobic composting of organic waste material, a first recirculation means for recirculating gases extracted from the or each vessel to a first storage means and a second recirculation means for recirculating water extracted from the or each vessel to a second storage means or an interconnected vessel, wherein the organic waste material in the interconnected vessel is undergoing anaerobic digestion.

BRIEF DESCRIPTION OF THE DRAWINGS

The present invention will now be described, by way of example only, with reference to the accompanying drawings, in which:—

DETAILED DESCRIPTION OF THE PREFERRED EMBODIMENT

Figure 1:
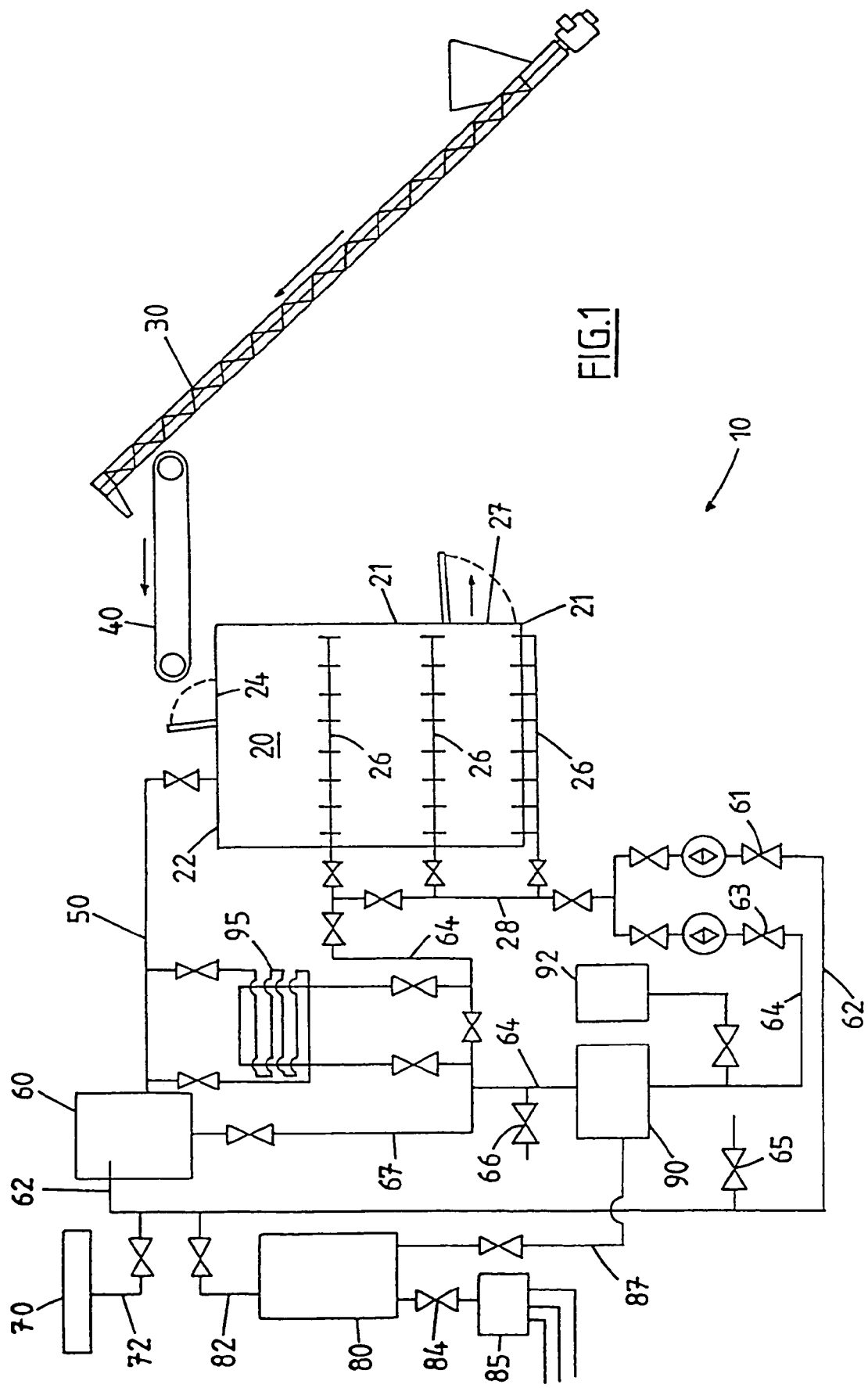
FIG. 1 is a schematic diagram of an apparatus, arranged in use, to house organic waste material and to facilitate therein a sequential decomposition process comprising an anaerobic digestion stage and an aerobic composition stage, in accordance with the present invention.

In FIG. 1 of the accompanying drawings there is shown an apparatus 10, arranged in use, to house organic waste material and to facilitate a sequential decomposition process, comprising an anaerobic digestion stage and an aerobic composting stage, therein.

The apparatus 10 includes an air tight pressurised vessel 20, arranged, in use, to house organic waste material. Preferably, the vessel 20 is constructed from a rigid, chemically inert material with good structural integrity such as steel or concrete. Preferably, the vessel 20 operates in a pressure range of between about 1–1000 kPa above atmospheric pressure.

An uppermost wall 22 of the vessel 20 is provided with a receival hatch 24 which is arranged in use to remain in an open position when organic waste material is loaded or unloaded from the vessel 20. The receival hatch 24 is arranged in use to remain in a closed position when the organic waste material is undergoing the sequential decomposition process.

The organic waste material may be loaded into the vessel 20 by an auger loader 30 and a belt conveyor 40 as shown in FIG. 1. It will be appreciated, however, that any convenient conveying and loading system may be used to load the vessel 20 with organic waste material.

The vessel 20 is also provided with an extraction hatch 27 which is disposed in a wall 21 of the vessel 20. The extraction hatch 27 is arranged in use to remain in an open position when an end product of the sequential decomposition process is unloaded from the vessel. The extraction hatch 27 is arranged in use to remain in a closed position during the sequential decomposition process.

The vessel 20 is provided with a plurality of feeder lines 26 which are arranged, in use, to deliver air or water to the vessel 20. It is envisaged that air will be delivered to the vessel 20 under a positive pressure of between about 1–1000 kPa above atmospheric pressure. It has been found that operating air pressures inside the vessel of about between 1–1000 kPa above atmospheric pressure facilitate a more efficient air penetration and distribution of air into the material contents of the vessel 20. The feeder lines 26 are also arranged to drain the vessel 20 of excess water under negative pressure. The feeder lines 26 are disposed in at least one wall 21 of the vessel 20 such that the water or the air is evenly distributed in the organic waste material housed by the vessel 20. The even distribution of water or air eliminates the necessity for an agitation means within the vessel 20 homogenise conditions therein. It is envisaged, however, that in the case of a large industrial scale operation where the volume of the vessel 20 is very large, it may be more convenient to install an agitation means within the vessel 20 to assist homogenise conditions therein The feeder lines 26 are connected with a control line 28 which is arranged to control the flow and distribution of water and air to and from the vessel 20 at appropriate stages of the sequential decomposition process.

In an alternative embodiment of the invention the vessel 20 is provided with at least one elongate perforated lance which is also arranged in use to deliver air or water to the vessel 20 in a similar manner to the feeder lines 26. It is envisaged that the perforations will be equidistantly spaced apart from one another over the length of the lance in order to promote even distribution of air and water into the vessel 20. The lance is arranged to depend from the uppermost wall 22 or the lowermost wall 21 of the vessel 20. The vessel 20 is additionally provided with a drainage means to drain excess water from the vessel 20 under negative pressure.

The apparatus 10 is provided with a first and a second recirculation lines 62, 64. The first recirculation line 62 is provided with a first pump 61 which is arranged to facilitate recirculation of gas through the apparatus 10. Air from an external source may also be received into the first recirculation line 62 via a first port 65. The second recirculation line 64 is provided with a second pump 63 which is arranged to facilitate recirculation of water though the apparatus 10. Water from an external source may also be received into the second recirculation line 64 via a second port 66. The second port 66 is also arranged to receive biological or chemical additives, such as a bacterial inoculum, enzymes and pH buffers.

The first and second recirculation lines 62, 64 are interconnected with the vessel 20 by the control line 28 and the feeder lines 26.

The uppermost wall 22 of the vessel 20 is also provided with a gas extraction line. The gas extraction line 50 interconnects the vessel 20 and a de-watering tank 60. The gas extraction line 50 is arranged, in use, to extract gases generated in the interior of the vessel 20 during an anaerobic digestion stage of the sequential decomposition process, or to extract air from the head space of the vessel 20 during an aerobic composting stage of the sequential decomposition process.

The de-watering tank 60 is arranged, in use, to remove water from the extracted gases. The de-watering tank 60 is connected with the first recirculation lines 62 and a de-watering line 67. In this way, the first recirculation line 62 facilitates the recirculation of de-watered gas through the apparatus 10. The de-watering line 67 is arranged in use to recirculate the water which has been removed from the gas through the apparatus 10. The de-watering line 67 is connected to the second recirculation line 64.

The apparatus 10 is provided with a biofilter 70 which is interconnected with the first recirculation line 62 by an exit line 72. The biofilter 70 is arranged in use to scrub the recirculating air of odorous emissions resulting from the anaerobic digestion and aerobic composting stages of the sequential composting process prior to exhaustion of the scrubbed recirculating air into the atmosphere.

The apparatus 10 is also provided with a gas storage tank 80 which is interconnected with the first recirculation line 62 by a first storage line 82. The gas storage tank 80 is arranged in use to receive biogas, predominantly a mixture of methane and carbon dioxide, generated during the anaerobic digestion stage of the sequential decomposition process. It will be understood that the received biogas will have been treated in the de-watering tank 60 prior to storage in the gas storage tank 80.

The gas storage tank 80 is interconnected with a power generator 85 by a generator line 84. The power generator 85 is arranged to convert the biogas to electrical power, wherein the electrical power may be distributed to other components of the apparatus 10 as required. Any excess electrical power generated by the generator 85 could be delivered to an external power grid.

As shown in FIG. 1, the apparatus 10 also includes a water heater tank 90. The water heater tank 90 is interconnected with the de-watering tank 60 by the de-watering line 67. The water heater tank 90 is arranged to receive water from the de-watering tank 60 via the de-watering line 67 and from the second port 66. The water heater tank 90 is also interconnected with the gas storage tank 80 by a first delivery line 87. The water heater tank 90 is provided with means to convert the biogas received from the first delivery line 87 to heat in order to control the temperature of the water in the water heater tank 90. It will be understood that water in the water heater tank 90 is maintained at a temperature of 15° C. to 75° C. The water is arranged, in use, to be recirculated through the apparatus 10 via the second recirculation line 64, the control line 28 and the feeder lines 26 into the vessel 20 during the anaerobic digestion stage of the sequential decomposition process. Delivery of water heated to a temperature range at which anaerobic microbial activity is optimised assists the anaerobic digestion stage of the sequential decomposition process. As shown in FIG. 1, the apparatus 10 also includes a water storage tank 92. The water storage tank 92 is connected to the second recirculation line 64. The water storage tank 92 is arranged to receive and store water extracted from the vessel 10 after completion of the anaerobic digestion stage of the sequential decomposition process.

The apparatus 10 is also provided with a heat exchange means 95 which is connected with the gas extraction line 50. The heat exchange means 95 is arranged in use to utilise energy from hot air extracted during the aerobic composting stage. The energy from the extracted hot air is used to heat water flowing through the second recirculation line 64. It will be appreciated that the extracted hot air may also be recirculated through the apparatus 10 via the first recirculation line 62, the control line 28 and the feeder lines 26 into the vessel 20 before the commencement of the anaerobic digestion stage in order to heat the organic waste material therein. Preheating the organic waste material to a temperature range of between 15° C. and 75° C. at which anaerobic microbial activity is optimised assists the anaerobic digestion stage of the sequential decomposition process. It will be understood that the heat exchange means 95 operates most efficiently when included in a plant where a plurality of vessels 10 are configured in a sequential batch configuration.

Figure 2:
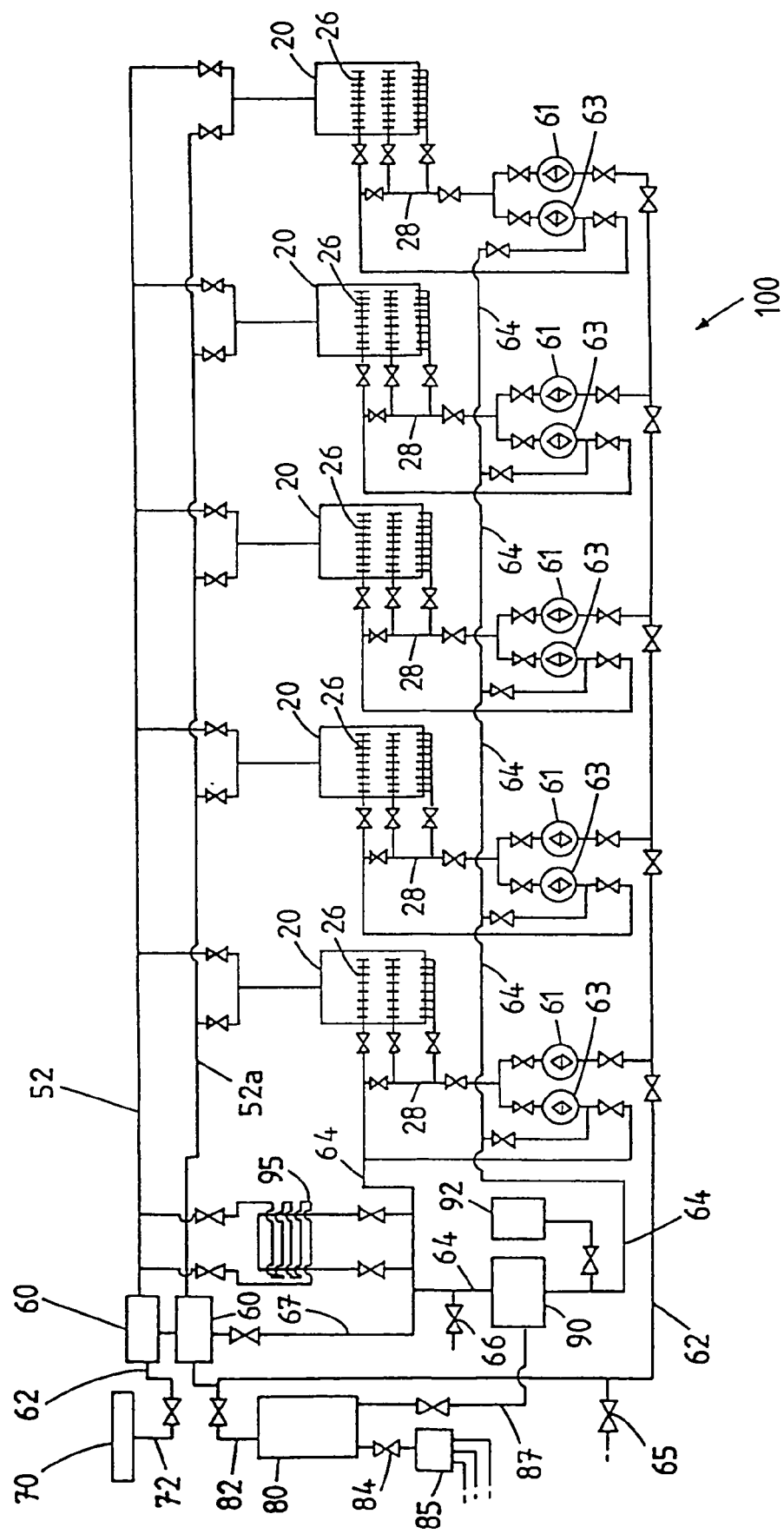
FIG. 2 is a schematic diagram of a plurality of vessels shown in FIG. 1, interconnected by a first and second recirculation means, wherein each vessel is arranged, in use, to house organic waste material and to facilitate a sequential decomposition process therein, and the first and second recirculation means is arranged, in use, to recirculate byproducts from each vessel to an adjoining vessel in accordance with the present invention.

In FIG. 2 of the accompanying drawings there is shown an apparatus 100 including a plurality of vessels 20 as described in FIG. 1 wherein like numerals and symbols refer to like parts throughout. The vessels 20 are interconnected with one another by the first and second recirculation lines 62 and 64

In addition to the functions of the first recirculation line 62 previously described in relation to FIG. 1, the first recirculation line 62 is also arranged to facilitate recirculation of gas extracted from one vessel 20 to the control line 28 and feeder lines 26 of another vessel 20. For example, hot air extracted from one vessel undergoing the aerobic composting stage can be recirculated to another vessel 20 which may require heat to initiate the aerobic composting stage. Alternatively, the organic waste material housed by another vessel 20 may be heated by the recirculated hot air before commencement of the anaerobic digestion stage in that vessel 20.

In addition to the functions of the second recirculation line 64 previously described in relation to FIG. 1, the second recirculation line 64 is arranged to facilitate recirculation of water removed from one vessel 20 to the control line 28 and feeder lines of another vessel 20. For example, water removed from one vessel 20 after completion of the anaerobic digestion stage can be recirculated to another vessel 20 which may require an increased water content to commence the anaerobic digestion stage.

It will be appreciated that the contents of each vessel 20 may be at varying stages of the sequential decomposition process. Preferably, each vessel 20 is configured to form a sequential batch to facilitate continuous operation of the sequential decomposition process of the present invention.

A multiple vessel system is configured such that one vessel 20 is filled with organic waste material while another is being emptied, the remaining vessels 20 in the multiple vessel system 100 being arranged to be at various stages of the sequential decomposition process.

It will also be appreciated that additional vessels 20 may be interconnected to the apparatus 100 by the first and second recirculation lines 62 and 64 to increase processing volumes of the apparatus 100.

As shown in FIG. 2, there is provided a gas extraction line 52 for air removed from each vessel 20 during the aerobic composting stage, and an additional gas extraction line 52*a* for the extraction of biogas from the contents of each vessel 20 which are generated during the anaerobic digestion stage.

The sequential decomposition process of organic waste material will now be described with reference to the apparatus 10 as shown in FIG. 1 and the apparatus 100 as shown in FIG. 2.

The sequential decomposition process of organic waste material is a two stage process including an anaerobic digestion stage followed by an aerobic composting stage. Preferably, the organic waste material undergoes a preliminary aerobic composting pre-conditioning stage followed by a preliminary digestion pre-conditioning stage before commencement of the anaerobic digestion stage and the aerobic composting stage.

The organic waste material is typically sized and mixed to effect a substantially homogenous mixture. It is understood that organic waste material refers to solid organic waste material, comprising vegetable matter; household and municipal organic waste, including cellulosic material such as waste paper; industrial organic waste; and agricultural organic waste, for example animal manures. Typically, the C:N ratio of the organic waste material is greater than 20. Consistency of the material is preferably optimised for optimum water flow through the contents in the vessel 20 during the preliminary anaerobic digestion pre-conditioning stage and the anaerobic digestion stage, and optimum air flow through the contents in the vessel 20 during the preliminary aerobic composting pre-conditioning stage and the aerobic composting stage. The receival hatch 24 of the vessel 20 is opened, and the auger loader 30 and belt conveyor 40 deliver the homogenised waste material into the vessel 20 until the vessel 20 is substantially full. The receival hatch 24 is then closed to seal the vessel 20.

The preliminary aerobic composting pre-conditioning stage comprises the steps of:
1) adjusting the moisture content of the waste material to 40–60% of the wet weight (w/w);
2) pumping air into waste material in the vessel 20; and
3) decomposition of the waste material by aerobic bacteria.

Water from an external source at the second port 66 is pumped by the second pump 63 through the second recirculation line 64 and into the vessel 20 via the control line 28 and the feeder lines 26. The feeder lines 26 evenly distribute the water through the organic waste material such that the moisture content of the waste material ranges from 40–60% wet weight (w/w) throughout the contents of the vessel 20. Alternatively, the moisture content may be adjusted prior to loading the vessel 20 with the waste material.

Air from an external source at the first port 65 is then pumped under pressure within the range 1–1000 kPa above atmospheric pressure by the first pump 61 through the first recirculation line 62 of the apparatus 10 and into the vessel 20 via the control line 28 and the feeder lines 26. The feeder lines 26 evenly distribute the air through the organic waste material such that the organic waste material is substantially evenly aerated.

It will be appreciated that initially during the preliminary aerobic pre-conditioning composting stage air is optionally extracted from the headspace in the vessel 20 between the organic waste material and the uppermost wall 22 of the vessel 20, via the gas extraction line 50. The extracted air may optionally have water removed therefrom in the dewatering tank 60 before the air is pumped through the first recirculation line 62 by the first pump 61 back into the vessel 20.

Alternatively, air extracted by the means described above may be sourced from another vessel 20.

Under the conditions described above, indigenous aerobic bacteria present in the organic waste material begin to metabolise and break down the organic waste material. The preliminary aerobic composting pre-conditioning stage operates in a temperature range of 15° C. to 75° C. for a period between 1 to 28 days.

The purpose of the preliminary aerobic composting pre-conditioning stage is to raise the temperature of the contents of the vessel 20 to a temperature within a range of 15° C.–75° C., preferably over 50° C. The temperature range of 15° C.–75° C. is a preferred range in which the preliminary anaerobic digestion pre-conditioning stage and the anaerobic digestion stage proceeds at optimum efficiency. In this way, the present invention avoids the necessity of reliance on a fuel driven heating means to raise the temperature of the contents within the vessel 20 to the optimal temperature for commencement of the preliminary anaerobic digestion pre-conditioning stage and/or the anaerobic digestion stage.

Preferably, the preliminary aerobic composting pre-conditioning stage comprises creating conditions under which the contents of the vessel 20 undergoes aerobic composting. Heat generated by the aerobic composting of the contents of the vessel 20 raises the ambient temperature thereof to a temperature range of 15° C.–75° C. at which point the conditions within the vessel 20 are changed by an operator such that the preliminary anaerobic digestion pre-conditioning stage or the anaerobic digestion stage commences. It will be understood that other suitable alternative means to raise the temperature of the contents of the vessel 20 may be substituted for the preliminary aerobic composting pre-conditioning stage. For example, heated air or steam from a convenient accessible geothermal source may be pumped into the contents of the vessel 20 to raise the temperature therein to the desired range for commencement of the preliminary anaerobic digestion pre-conditioning stage. Alternatively, referring to the apparatus 100 in FIG. 2, heated air extracted from a vessel 20 in which the contents are undergoing the aerobic composting stage may be re-circulated to another vessel 20 via the first recirculation line 62 in order to heat the contents of that vessel 20 to a desired temperature range.

The preliminary anaerobic digestion pre-conditioning stage comprises the steps of:

1) sealing the vessel 20 to prevent ingress of air into the vessel 20, and 2) depletion of oxygen in the sealed vessel 20.

The vessel 20 is sealed when the temperature of the contents of the vessel 20 is in the range of 15° C.–75° C., preferably greater than or equal to 50° C. It is well understood that temperatures in the range of 15° C.–75° C. are desirable for anaerobic digestion operating conditions. The vessel 20 is sealed by ceasing to pump and/or circulate air through the feeder lines 26 and the control line 28 to the vessel 20.

Oxygen levels will eventually be depleted in the sealed vessel 20 by action of the aerobic bacteria therein. Typically, the metabolic processes of the aerobic bacteria converts the oxygen to carbon dioxide. When the oxygen levels in the vessel 20 are sufficiently depleted, the anaerobic digestion stage of the sequential decomposition process commences.

The purpose of the preliminary anaerobic digestion pre-conditioning stage is to facilitate the depletion of oxygen inside the vessel prior to addition of an anaerobic inoculum and the commencement of the anaerobic digestion stage.

Biogas is produced at the commencement of and during the anaerobic digestion stage. A mixture of methane and oxygen in the vessel 20 would provide a combustible and potentially explosive gas mixture. Furthermore, the introduction of an anaerobic innoculum into a vessel 20 having a moderate to high oxygen level would prove fatal to the anaerobic inoculum since most anaerobic bacteria are intolerant to oxygen.

Thus, it is an advantage of the preliminary anaerobic digestion pre-conditioning stage to deplete oxygen levels in the sealed vessel 20 before commencement of the anaerobic digestion stage.

When the oxygen level drops to below accepted standards the anaerobic digestion stage of the sequential decomposition process can commence.

The anaerobic digestion stage comprises the steps of:

1) adjusting the moisture content of the waste material to 50–95% wet weight (w/w); and 2) digestion of the waste material by anaerobic bacteria.

Water from an external source at the second port 66 is received through the second recirculation line 64 and pumped by the second pump 63 into the vessel 20 via the control line 28 and the feeder lines 26. The feeder lines 26 evenly distribute the water through the organic waste material such that the moisture content of the waste material ranges from 50–95% wet weight (w/w) throughout the contents of the vessel 20. It will be appreciated that the water from the external source may have been mixed with a bio-sludge to act as an anaerobic bacterial inoculum. Alternatively, water removed from another vessel 20 which has undergone the anaerobic digestion stage may be recirculated by the second recirculation line 64 into the present vessel 20. In this way, process water from one anaerobic digestion can be used to inoculate the contents of an interconnected vessel 20 undergoing the anaerobic digestion stage in a multiple vessel system 100.

The anaerobic digestion stage operates in a mesophilic to thermophilic temperature range between 15° C.–75° C., preferably over 50° C. for a period between 4 to 20 days. Methane and carbon dioxide gases are generated during the anaerobic digestion stage. They are extracted under pressure through the gas extraction line 50 and delivered to the de-watering tank 60 where water is removed from the extracted gases. The extracted gases are then delivered through the first recirculation line 62 to the gas storage tank 80 via the first storage line 82. The gas may then be converted to electrical power by the power generator 85, or alternatively, used to heat water in the water heater tank 90.

The water which is removed from the extracted gases in the de-watering tank 60 is then delivered to the heater tank 90 by the de-watering line 67. The water may be heated in the water heater tank 90. The heated water may also be recirculated by the second recirculation line 64, the control line 28 and the feeder lines 26 back into the vessel 20 for a subsequent anaerobic digestion stage, of another batch of organic waste material. In this way the heat and electricity indirectly generated by the anaerobic digestion stage can be utilised to subsidise energy requirements in interconnected vessels 20 or used in subsequent stages of the sequential decomposition process occurring at a later time in the same vessel 20. It has been found that during the anaerobic digestion stage the amount of volatile solids is reduced and nitrogen content in the contents of the vessel 20 is concentrated.

Following completion of the anaerobic digestion stage conditions within the vessel 20 are altered such that the aerobic composting stage may commence.

The aerobic composting stage comprises the steps of:

1) reducing moisture content within the vessel; and 2) aerating the contents of the vessel.

Excess water is removed from the vessel 20 via the feeder lines 26 and the control line 28 under gravity drainage combined with application of a negative pressure to draw excess water into the second recirculation line 64. Thus, the moisture content of the contents within the vessel 20 is adjusted to 40 to 60% w/w. It will be appreciated that the moisture content can also be lowered to the desired range by pumping warm air sourced from another vessel 20 in a multiple vessel system 100 undergoing aerobic composting through the control line 28 and the feeder lines 26 into the vessel 20. The excess water is recirculated into the water storage tank 92. Alternatively, the excess water may be recirculated by the second recirculation line 64 into another vessel 20 in a multiple vessel system 100 whose contents are about to undergo the anaerobic digestion stage.

The contents of the vessel 20 are aerated by pumping air through the control line 28 and the feeder lines 26 into the vessel 20. It will be appreciated that the conditions for the aerobic composting stage are the same as for the preliminary aerobic composting pre-conditioning stage described previously.

Adjustment to the operating parameters may be made by dosing the vessel contents through the second port 66 as previously described.

It will be appreciated that heat generated from the aerobic composting stage may be used to facilitate the formation of mesophilic to thermophilic conditions for an anaerobic digestion stage or an aerobic composition stage occurring in another interconnected vessel 20.

Upon completion of the aerobic composting stage, the resulting compost will be deposited from the vessel 20 through the extraction hatch 27, loaded and packed for sale.

The resulting compost is relatively dry and has little odour. Nitrogen content in the resulting material is fixed as ammonium. Typically, the C:N ratio of the resulting compost is $\leq 20$.

The present invention will now be further illustrated with reference to the following Example.

EXAMPLE

Organic waste material consisting of shredded newspaper (6.75 kg), shredded cardboard (6.75 kg), grass clippings (4.4 kg), garden waste (30.4 kg) and chicken manure (38.3 kg) was blended and received in a 0.8 $m^3$ vessel. The C:N ratio of the organic waste material was 25.6.

The contents of the vessel were subjected to a preliminary aerobic composting pre-conditioning stage wherein air was administered to the contents of the vessel at a flow rate of 300 L/hr. Interior air pressure inside the vessel was maintained at 25 kPa above atmospheric pressure. The temperature of the contents of the vessel rose to 52° C. after a period of three days, whereupon the administration of air to the contents of the vessel was discontinued.

The contents of the vessel were then subjected to conditions under which anaerobic digestion occurs. A liquid digestate derived from an earlier anaerobic digestion of a previous batch of organic waste material was delivered to the vessel. Recirculation of the liquid digestate through the vessel was operated continuously for a period of 8 days. Biogas was generated after a short period. The volume of biogas generated during the anaerobic digestion stage peaked at about 9 $m^3/m^3 \cdot day$ with an average production rate of 7 $m^3/m^3 \cdot day$. The average methane content of the biogas varied from 40–60%.

Following anaerobic digestion, the liquid digestate was drained from the vessel and air was administered to the vessel at a flow rate of 150 L/hr. Interior air pressure inside the vessel was maintained at 25 kPa above atmospheric pressure. Conditions for aerobic composting were maintained for five days.

After five days the resulting compost was removed from the vessel. Internal temperatures of the compost were monitored for four consecutive days to assess the stability of the compost. The internal temperature did not exceed 24° C., thus indicating desired stability.

The compost was analysed for key parameters corresponding to requirements of Australian Standards AS 4454-2000 Composts, Soil Conditioners and Mulches. The results and comparative results are shown in the following Table. The C:N ratio of the resulting compost was 19.

TABLE

| Characteristic (units) | AS 4454-2000 requirements | Compost |
|---|---|---|
| P (% dry mass) | N/A | 0.6 |
| Nitrogen-ammonium (mg/L in extract) | <300 | 170 |
| Nitrogen-nitrate (mg/L in extract) | >100 (if plant nutrition claimed) | 175 |
| Total N (% dry matter) | $\geq 0.8$ if plant nutrition claimed | 1.3 |
| C:N ratio | <20 | 19 |
| Total C (% dry matter) | $\geq 25$ | 25 |
| Temperature | $\leq 40°$ C. for four days | 23° C. |

Modifications and variations as would be apparent to a skilled addressee are deemed to be within the scope of the present invention.

The invention claimed is:

1. An organic waste material treatment process for organic waste material received in a vessel comprising the sequential steps of:
   a) subjecting contents of the vessel to conditions under which preliminary aerobic pre-conditioning of the contents of the vessel proceeds and the temperature of the contents of the vessel is raised to at least 50° C.;
   b) sealing the vessel after step a) to prevent ingress of air thereto so that aerobic bacteria in the vessel cause the oxygen content thereof to be depleted, wherein metabolic processes of the aerobic bacteria convert oxygen to carbon dioxide;
   c) adjusting water content of the contents of the vessel after step b) to 50 to 95% wet weight;
   d) simultaneously with or subsequently to step c) adding an anaerobic bacterial inoculum to the contents of the vessel;
   e) anaerobically digesting the contents of the vessel after steps c) and d);
   f) separating gaseous byproducts resulting from step e);
   g) reducing the water content of residual material in the vessel;
   h) evenly distributing air to the residual material in the vessel to create conditions suitable for aerobic composting of the residual material to proceed without agitating the contents of the vessel at a pressure of between 1–1000 kPa above atmospheric pressure to ensure even penetration of the residual material by the air;
   i) aerobically composting the residual material by action of aerobic bacteria; and
   j) recovering compost resulting from step i) from the vessel.

2. The organic waste material treatment process according to claim 1, wherein air is administered to the contents of the vessel in step a) at a pressure of between 1–1000 kPa above atmospheric pressure to ensure even penetration of the contents of the vessel by the air.

3. The organic waste material treatment process according to claim 2, wherein air is administered to the contents of the vessel at a pressure of between 5–50 kPa above atmospheric pressure to ensure even penetration of the contents of the vessel by the air.

4. The organic waste material treatment process according to claim 3, wherein air is administered to the contents of the vessel at about 25 kPa above atmospheric pressure.

5. The organic waste material treatment process according to claim 1, wherein air is administered to the residual material at step h) at a pressure of between 5–50 kPa above atmospheric pressure to ensure even penetration of the residues by the air.

6. The organic waste material treatment process according to claim 5, wherein air is administered to the residual material at step h) at a pressure of about 25 kPa above atmospheric pressure to ensure even penetration of the residues by the air.

7. An organic waste material treatment process for organic waste material received in a plurality of interconnected vessels comprising the steps of:
   a) subjecting the contents of the or each vessel to conditions under which preliminary aerobic pre-conditioning of contents of the vessel proceeds in order to raise the temperature of the contents of the vessel to at least 50° C.;
   b) sealing the or each vessel after step a) to prevent ingress of air thereto so that aerobic bacteria in the or each vessel cause the oxygen content thereof to be depleted, wherein metabolic processes of the aerobic bacteria convert oxygen to carbon dioxide;
   c) adjusting water content of the contents of the or each vessel after step b) to 50 to 95% wet weight;
   d) simultaneously with or subsequent to step c) adding water received from an interconnected vessel to the or each vessel to create conditions suitable for anaerobic digestion of the contents to proceed in the or each vessel, whereby contents of the interconnected vessel have already undergone anaerobic digestion and the water contains an anaerobic bacterial inoculum;
   e) anaerobically digesting the contents of the or each vessel after steps c) and d);
   f) separating gaseous by-products resulting from step e);
   g) removing at least a portion of the water from the or each vessel and transferring the removed portion of the water to another interconnected vessel for use in step d);
   h) evenly distributing air to residual material in the or each vessel to create conditions suitable for aerobic composting of the residual material to proceed without agitating the contents of the vessel at a pressure of between 1–1000 kPa above atmospheric pressure to ensure even penetration of the residual material by the air;
   i) aerobically composting the residual material by action of aerobic bacteria; and
   j) recovering compost resulting from step i) from the or each vessel.

8. The organic waste material treatment process according to claim 7, wherein air is administered to the contents of the or each vessel in step a) at a pressure of between 1–1000 kPa above atmospheric pressure to ensure even penetration of the contents of the or each vessel by the air.

9. The organic waste material treatment process according to claim 8, wherein air is administered to the contents of the or each vessel at a pressure of between 5–50 kPa above atmospheric pressure to ensure even penetration of the contents of the or each vessel by the air.

10. The organic waste material treatment process according to claim 9, wherein air is administered to the contents of the or each vessel at about 25 kPa above atmospheric pressure.

11. The organic waste material treatment process according to claim 7, wherein air is administered to the residual material at step h) at a pressure of between 5–50 kPA above atmospheric pressure to ensure even penetration of the residues by the air.

12. The organic waste material treatment process according to claim 11, wherein air is administered to the residues at step h) at a pressure of about 25 kPa above atmospheric pressure to ensure even penetration of the residues by the air.

* * * * *